United States Patent
Pouletty et al.

[11] Patent Number: 5,534,412
[45] Date of Patent: Jul. 9, 1996

[54] ALLOANTIGEN ENHANCEMENT ASSAY

[75] Inventors: Philippe Pouletty, Atherton; Chin-Hai Chang, Los Altos, both of Calif.

[73] Assignee: SangStat Medical Corporation, Menlo Park, Calif.

[21] Appl. No.: 315,203

[22] Filed: Sep. 29, 1994

Related U.S. Application Data

[63] Continuation-in-part of Ser. No. 961,579, Oct. 16, 1992, abandoned, which is a continuation-in-part of Ser. No. 745,163, Aug. 15, 1991, abandoned, which is a continuation-in-part of Ser. No. 698,319, May 10, 1991, Pat. No. 5,256,543.

[51] Int. Cl.$^6$ ............... G01N 33/536; G01N 33/543
[52] U.S. Cl. ............... 435/7.24; 435/7.9; 435/7.94; 435/962; 435/967; 436/518; 436/531; 436/536
[58] Field of Search ............... 435/7.24, 7.9, 435/7.94, 962, 967; 436/518, 531, 536

[56] References Cited

U.S. PATENT DOCUMENTS 5,420,013  5/1995  Pouletty et al. ............... 435/7.24

OTHER PUBLICATIONS

Albrecht, J. and Muller, H. A. G., Clin. Chem, (1987), 33:1618–1623. HLA–B27 Typing by Use of Flow Cytofluorometry.

Thorsby, E., et al., Tissue Antigens, (1983), 21:148–158. HLA–D Restriction of Antigen–Specific Proliferative T Cell Responses.

Sakaguchi, K., et al., Human Immunology, (1988), 21:193–207. Anti-HLA–B7, B27, Bw42, Application for a Double Beerminant Immunoassay.

Ferreira, A., et al., Clin. Chem. Acta, (1988), 174:207–212. Quantification of Soluble Serum HLA Class 1 Antigens in Healthy Volunteers and AIDS Patients.

Davies, H. FF. S., et al., Transplantation, (1989), 47:524–527. Soluble HLA Antigens in the Circulation of Liver Graft Recipients.

Hill, A. V. S., et al., Lancet, (1991), 337:640–642. HLA Class 1 Typing by PCR:HLA–B27 and an African B27 Subtype.

Doxiadis, I. and Grosse–Wilde, H., Vox Sang, (1989), 56:196–199. Typing for HLA Class 1 Gene Products Using Plasma as Source.

Hansen, T. and Hannestad, K., Tissue Antigens, (1987), 30:198–203. Simple Rosette Assay for HLA–B27 Typing of Whole Blood Samples.

Thurau, S. R., et al., Tissue Antigens, (1989), 33:511–519. Expression and Immunogenicity of HLA–B27 in High Transfection Recipient P815:a New Method to Induce Monoclonal Antibodies Directed Against HLA–B27.

Villar, L. M., et al., Eur. J. Immunol., (1989), 19:1835–1839. Detection of Soluble Class 1 Molecules (non HLA–A or HLA–B) in Serum, Spleen Membranes and Lymphocytes in culture.

Wu, D. Y., et al., DNA, (1989), 8:135–142. Direct Analysis of Single Nucleotide Variation in Human Dna and Rna Using in Situ Dot Hybridication.

Trapani, J. A., et al., Immunol. Cell Biol. (1988), 66:215–219. Immunoradiometric Assay for the Rapid Detection of HLA–B27.

*Primary Examiner*—David Saunders
*Attorney, Agent, or Firm*—Bertram I. Rowland; Pamela J. Sherwood

[57] ABSTRACT

Methods and compositions are provided for the determination of cross-reactive alleles, where there is no antibody which will specifically distinguish between the two alleles. Particularly, the method employs an antibody which binds to the two alleles bound to a surface, an antibody specific for one of the alleles, a labeled conjugate which binds to a consensus sequence present in both alleles and positive and negative controls. By having an enhanced value where the interfering allele is present as compared to a value for the target allele, one can distinguish between the various alternatives involving the presence or absence of one or both alleles.

9 Claims, 1 Drawing Sheet

ALLOANTIGEN ENHANCEMENT ASSAY

CROSS-REFERENCE TO RELATED APPLICATIONS

This application is a continuation-in-part of application Ser. No. 961,579, filed Oct. 16, 1992 and now abandoned, which was a continuation-in-part of application Ser. No. 745,163, filed Aug. 15, 1991 and now abandoned, which was a continuation-in-part of application Ser. No. 698,319, filed May 10, 1991 and now U.S. Pat. No. 5,256,543.

TECHNICAL FIELD

The technical field of this invention is HLA typing.

BACKGROUND

There is substantial interest in being able to type human leukocyte antigens (HLAs) for a variety of reasons. In many situations it has been found that specific HLA alleles may be associated with a susceptibility to a particular disease. For example, HLA-B27 has been associated with ankylosing spondylitis and related diseases. When transplanting organs to a host it is desirable that the organs be matched, so as to minimize the risk of rejection. HLA typing may also find application is determining lineage, epidemiology and the like.

There is an extensive family of HLA antigens divided into Class I and Class II. In each of the classes, them are polymorphic regions. These polymorphisms may or may not provide for epitopes which will induce an immune response, which will allow for the preparation of antisera or monoclonal antibodies which are specific for a specific HLA allele and able to distinguish that HLA allele from other HLA alleles.

This situation is exemplified by the cross-reactivity between HLA-B27 and HLA-B7 where monoclonal antibodies are not readily available which are specific for HLA-B27, and which do not cross-react with HLA-B7 or any other HLA alleles.

Since mammals are diploid, there will be always be two alleles present at every HLA locus. Thus, unless one can determine specifically a particular HLA allele, one cannot be certain whether there are two different alleles or one is observing cross-reactivity. There is, therefore, substantial interest in developing methods which will allow for the accurate detection of a particular HLA allele in those cases where substantial cross-reactivity is observed with other HLA alleles.

Relevant Literature

Sakaguchi et al. (1988) *Human Immunology* 21:193–207 describes the use of monoclonal antibodies in determination of HLA-B27 and a double determinant immunoassay for detection of HLA-B27. Villar et at. (1989) *Eur. J. Immunol.* 19:1835–1839 describe the detection of Class I molecules from a variety of sources. Doxiadis and Grosse-Wilde (1989) *Vox Sang* 56:196–199 describe the detection of HLA Class I proteins. Ferreira et al. (1988) *Clin. Chim. Acta.* 174:207–211 describe the use of a solid-phase enzyme immunoassay for detection of HLA Class I antigens in sera.

SUMMARY OF THE INVENTION

Methods and compositions are provided for detecting closely-related alleles employing immunoassays, where there is no available antibody to distinguish between two alleles. The methods and compositions find specific ,exemplification in relation to distinguishing the HLA alleles B27 and B7, where B27 is of diagnostic interest. The method employs an antibody cross-reactive with the two alleles bound to a surface, an antibody specific for one of the two alleles, but not the other, and a receptor for a conserved region of the two alleles, which receptor is conjugated to a label for detection. The method employs negative and positive controls to provide for detection of a minimal signal and an enhanced signal.

DESCRIPTION OF THE SPECIFIC EMBODIMENTS

Figure 1:
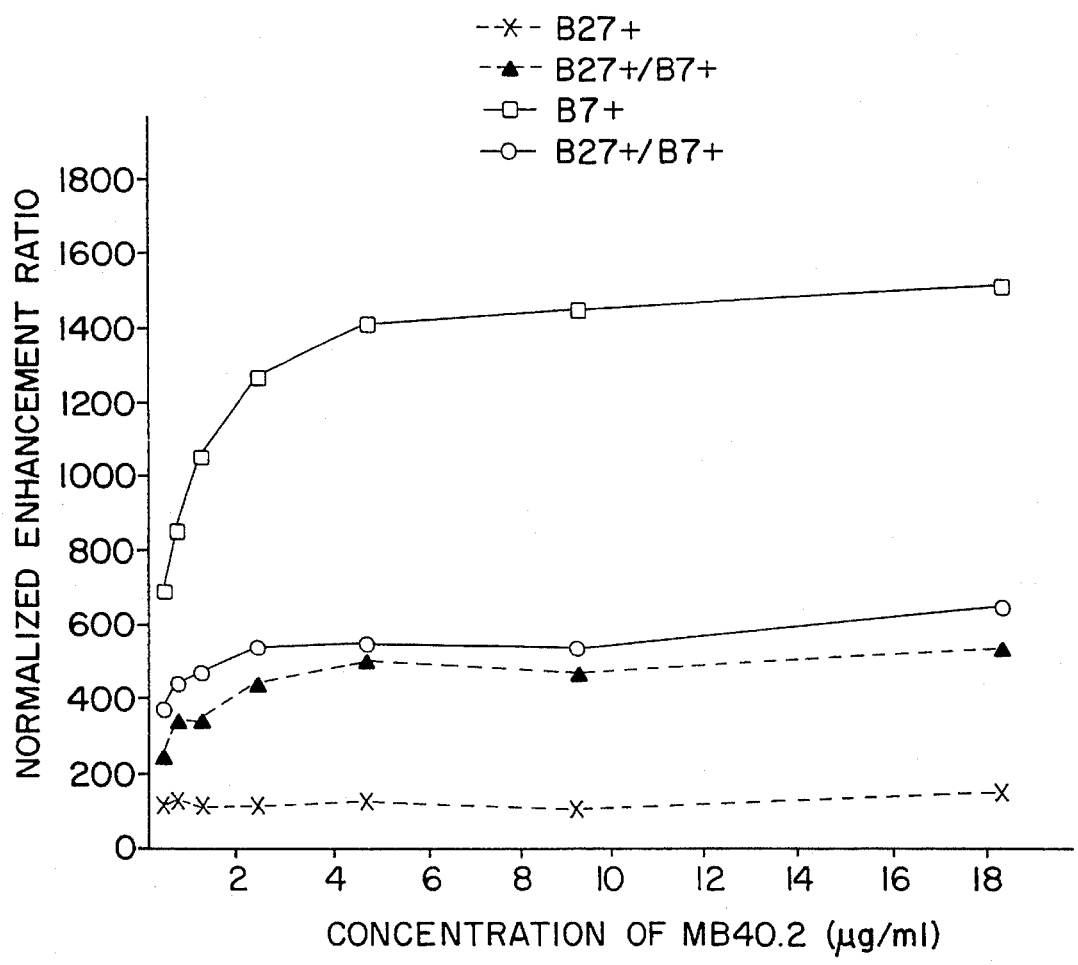
FIG. 1 is a graph demonstrating the effect of anti-B7 antibody concentration of enhancement of signal from samples containing B27 antigen and/or B7 antigen.

Methods and compositions are provided for the accurate detection and quantitation of one of two polymorphic antigens in a sample, where the antigens are characterized by having no useful receptor readily available to distinguish between the two antigens, the antigens are members of a much larger group of antigens, usually substantially in excess of 10, where there is substantial cross-reactivity between the antigens in sharing numerous epitopes, and differences between the antigens may be subtle, involving only one or a few amino acids.

The method involves having an antibody which is able to bind to the two cross-reactive soluble alleles, exemplified by HLA-B27, and -B7, where there is no antibody which can specifically distinguish B27 from B7; an antibody specific for the cross-reactive antigen which is not of interest, exemplified by B7; a positive control comprising B7; a negative control comprising buffer; and a conjugate which recognizes a conserved region for the two alleles or common epitope, where the conjugate comprises a label which allows for detection. The two antibodies, one specific for the antigen which is not of interest and the other cross-reactive for the two antigens, will not substantially cross-block in antigen binding.

The subject method has particular application for physiological samples, particularly blood or fractions thereof, e.g., serum and plasma, ("blood" intends blood and fractions thereof), more particularly associated with HLA antigens, particularly soluble antigens which may be found in blood. The sample may be subject to prior treatment, such as removal of cells in the case of blood to provide plasma or serum, dilution with buffer, or other treatment as appropriate. Conveniently, blood or serum may be used. The volume of the sample used will usually be about 5–250 µl usually 10–100 µl.

An antibody cross-reactive with the two alleles is bound to a support, which will usually result in binding of the detectable conjugate to the support in the presence of the alleles. The bound antibody will usually be sufficient to bind greater than about 50% of the cross-reacting alleles present in the sample aliquot used in the assay, based on the amount encountered in normal samples, and at equilibrium will usually bind less than about 100% of the antigen which is not of interest.

The antibody may or may not have equal affinity for the two alleles, preferably having a higher affinity for the allele of interest, preferably at least about a 25% higher affinity. In addition, either antisera or monoclonal antibody may be used, using antisera when available from multiparous women, or monoclonal antibody, as appropriate. Thus, where one wishes to determine the presence of B27, one would have an antibody which is cross-reactive with B27 and B7, for which no convenient antibody is available which can distinguish between the two. The antibody may be bound to the surface in any convenient manner, either covalently or non-covalently, so long as it is maintained bound to the support during the course of the assay. Methods for binding antibodies to supports are well-known in the literature and need not be described here.

Any convenient support maybe used, such as microtiler wells, slides, tubes, etc., where each of the individual determinations can be maintained independent of the other determinations and the label can be discretely determined.

In carrying out the determination, normally both a positive and negative control will be employed. The positive control will comprise a predetermined amount of HLA-B7, generally at a concentration in the range of about 10 ng/ml to 5 μg/ml, more usually in the range of about 50 ng/ml to 1 μg/ml. The positive control provides both a base value for the presence of HLA-B7, and an enhanced value, which will be described below. The negative control is buffer or any other medium, such as human serum, which should not affect the value obtained in relation to the presence of HLA-B7 or B27.

In order to distinguish between the possibilities of there being neither B7 nor B27, only B7 or B27, or both B7 and B27, anti-B7 is added to the sample and to some controls, but not others. The anti-B7/B27 antibody will normally have greater affinity for the allele of interest, B27, as compared to the allele not of interest, so that when B7 or B27 is in the sample, one will usually get a greater signal with B27. However, when B7 is present and one adds the enhancing anti-B7, the observed signal will substantially increase. Since one may use different sized aliquots of sample in the analyte determination as compared to the controls, observed values will be adjusted accordingly. The amount of anti-B7 which is added will generally range from about 100 ng/ml to 200 μg/ml, more usually 1 μg/ml to 50 μg/ml, based on a sample volume of about 100 μl to 1 ml. The amount of enhancing antibody added will usually not be a large excess.

In order to determine the presence of bound B7 and/or B27, a conjugate is used which binds to a consensus sequence or public epitope of the two alleles. In the case of Class I HLA, conveniently, an antibody specific for $\beta_2$-microglobulin may be employed. Alternatively, one may use an antibody for the constant region of the α chain or other polyallele sequence. While antibodies, particularly monoclonal antibodies, are the most convenient, any other receptor which binds specifically to Class I HLA may also be used. The volume of the conjugate solution will generally range from about 10–500 μl.

The label may be any convenient label which provides the desired degree of sensitivity. Commonly employed labels include enzymes, fluorescers, radioisotopes, and the like. Of particular interest are enzymes, where the enzyme has a substrate which provides for a colored product, particularly a colored product which can be readily detected in a spectrophotometer. The enzyme substrate solution may be varied widely, generally being the range of about 20–500 μl.

The assay medium will generally be buffered at a pH in the range of about 6–9. Various buffers may be employed, such as phosphate, Triis, MOPS, HEPES, and the like. The concentration of the buffer will generally be sufficient to maintain the desired pH, generally being from about 10 mM to about 0.5M.

In carrying out the assay, conveniently a container having a plurality of wells may be employed, where the wells are positioned in parallel rows. A device which fulfills the requirements of the subject determinations is a microtiter plate. As a first step, one adds a predetermined volume of the anti-B7 solution to a first set of rows, for discussion purposes, the even rows. One then adds to individual wells in the odd rows the negative calibrator and the positive calibrator, desirably having three wells for the negative calibrator and three wells for the positive calibrator, so that the values can be averaged. To the first set of even wells, the volume of the negative and the positive calibrators added will be less than the volume used for the second set of odd rows, the total volume of the anti-B7 medium and the calibrator mediums in each well being equal to the total volume of the negative calibrator and positive calibrator solutions added to wells in the second odd set of rows. To the remaining wells, both odd and even, sample is added in an amount so as to provide the same total volume in each well. The total volume will generally be in the range of about 25–500 μl, preferably in the range of about 50–200 μl, more particularly 100 μl . Thus, each of the wells will have the same volume as a result of combining the anti-B7 solution with calibrators or sample, or as the result of adding solely the calibrators or sample.

The assay mixtures are then incubated for sufficient time to ensure that reaction can occur between the various binding members. Desirably, the incubation will be at least about 30 min and not more than about 6 h, generally running from about 1 h to 3 h. The incubation may be at any convenient temperature, room temperature sufficing, and being preferred because of the convenience.

After completion of the incubation, each of the wells will be thoroughly washed, to ensure that there is substantially no non-specific binding of HLA antigen to the wells. The washing may be a single washing, but will normally be a repetitive washing of at least two times and not more than about eight times, it being found that about 3–6 times suffices, where the wash solution is at least about equal to the original volume of the assay mixture and not more than about 5 times the original volume of the assay mixture for each washing.

After completion of the washing, the conjugate is then added to each well, where the volume of the conjugate will generally be in the range of about 25–200 μl at a concentration of about 100 ng/ml to 10 μg/ml. The assay mixtures are then incubated for a second time, usually at least about 0.5 h and not more than about 3 h, generally from about 1–2 h. The individual assay mixtures are then washed a second time, substantially in the manner described previously, to ensure that is substantially no non-specific binding of the conjugate. After completion of the washing, a substrate solution is added to each well, generally providing a volume of about 25–200 μl. The mixture is then incubated for sufficient time for reaction to occur to provide for detectable signal. Usually, about 5–100 min will suffice, generally from about 20–60 min will suffice. At the end of the reaction time, the reaction is stopped by any convenient means, such as an enzyme inhibitor, a denaturant, or the like. Illustrative stop solutions include 1N HCl, $H_2SO_4$, $H_3PO_4$, or the like. Normally the inhibition of further reaction will be a solution, which will have a volume that does not unduly dilute the substrate solution, usually being not more than twice the volume of the substrate solution and not less than about 0.25 times the volume of the substrate solution. Each of the wells may then be read in accordance with the absorption spectrum of the product.

Where an enzyme is not employed as the label, the steps may be varied, since there will be no need to add a substrate solution. For example, with a fluorescer or radioisotope, after washing the assay mixture free of non-specifically bound conjugate, one may then read the fluorescence or radioactivity in accordance with conventional ways.

To determine whether B27 is present, one may average the readings for the negative and positive controls. One then calculates the percent enhancement for the positive control in each specimen by dividing the result obtained in the presence of anti-B7 by the result obtained in the absence of anti-B7 times 100.

Two values are then calculated, arbitrarily designated as DV1 and DV2. DV1 is a function of the negative control, and it provides a cutoff value that distinguishes between reactive and non-reactive samples. In general, DV1 will equal the OD of the negative control in the absence of enhancing antibody, plus a percentage of the OD of the positive control in the absence of enhancing antibody. The particular values will be dependent on the particular format of the assay. DV2 is proportional to the percent enhancement obtained with the positive control. As an example, for the assay described in the experimental section, DV1 is 2×OD of the negative control in the absence of enhancing antibody plus 20% OD of the positive control in the absence of enhancing antibody, and DV2 is 0.8×percent enhancement for the positive control.

The presence of the antigen of interest in a test sample is indicated when the signal value obtained from the test sample in the absence of enhancing antibody is greater than DV1; and the percent enhancement obtained from the test sample in the absence and presence of enhancing antibody is less than DV2.

Kits can be provided which comprise containers, e.g., microtiter plates, where the container walls are coated with the cross-reacting monoclonal antibody, an enhancing monoclonal antibody to one of the alleles, and a monoclonal antibody-label conjugate which binds to a public or common epitope of the two alleles. Optionally, one of the alleles may be provided for a control, particularly the allele to which the enhancing monoclonal antibody binds. For an enzyme label, substrate could also be included as well as stopping solution. Also, buffer may be included.

The following examples are offered by way illustration and not by way limitation.

EXPERIMENTAL

A. Reagents

Positive control (PC): Human serum or plasma reactive in the ELISA assay, 0.01% thimerosal. Lyophilized (3 ml).

Negative control (NC): Human serum or defibrinated plasma unreactive in the ELISA assay, 0.01% thimerosal, lyophilized [3 ml reconstituted].

B27 microtiler well strips: Microassay 96-well plate (Nunc) coated with murine monoclonal antibodies reactive with HLA B7 and B27 antibens [KS4].

Enhancing solution (ES): Aqueous solution of murine monoclonal to a human HLA-B7 antigen [MB-40] in PBS containing protein stabilizers and 0.01% thimerosal.

Anti-$\beta_2$ microglobulin conjugate: Commercially-available horseradish peroxidase labeled rabbit anti-human $\beta_2$-microglobulin, diluted in a diluent.

OPD tablet: 30 mg o-phenylene diamine dihydrochloride.

Substrate buffer: Aqueous solution of 0.05M phosphate-citrate buffer, pH 5.0 containing 0.1% $H_2O_2$, 0.01% thimerosal.

Wash solution (10X): Aqueous solution containing 0.1M phosphate, 0.05% TWEEN-20 and 0.01% thimerosal.

Stop solution:. 1N $H_2SO_4$.

Deionized water containing 0.01% thimerosal is used for reconstitution.

Note: Reconstitute PC with 1.5 ml water prior to use. If crystals form in the 10X wash solution, warm up in 37° C. incubator to dissolve it before use.

B. Protocol

1. Add 80 µl of the enhancing solution (ES) to all wells of the odd-numbered rows in the microtiter plate. Leave all wells of the even-numbered rows empty.

2. To the first odd-numbered row add 20 µl of negative control (NC) to the first three wells and 20 µl of positive control (PC) to the second three wells. Add 20 µl of each sample into one well for the remaining wells of all odd-numbered rows.

3. Immediately add 100 µl of NC and PC in triplicate to the corresponding wells in the first even-numbered row. Add 100 µl of each sample to the corresponding single well in all even-numbered rows. Incubate the plate at room temperature for 2 h. Begin timing after the last well has been added. Cover the plate to minimize evaporation loss.

4. Dilute appropriate amount of the 10X wash solution to 1X with deionized water and assemble it into the ELISA plate wash station (such as Bio-Tek EL-403 Auto Washer). Wash the plate 5 times with 325 µl of wash solution each time. If washing manually, fill wells to the top with wash solution for each cycle and remove the solution by aspiration or dumping into the sink.

5. Add 100 µl of anti-$\beta_2$ microglobulin conjugate to each well. Cover the plate and incubate at room temperature for 90 min.

6. Prepare the Substrate Solution: At about 5 min before the end of step 5 add one OPD tablet to 10 ml of the substrate buffer. Note: Substrate solution must be used within 15 min of preparation.

7. Wash the plate as in step 4.

8. Add 100 µl of the substrate solution prepared in step 6 to each well and incubate at room temperature for 30 min. Keep the plate covered in the dark.

9. Add 100 µl of stop solution to each well. The sequence and rate of addition of the stop solution must match the sequence and rate of addition of substrate in step 8.

10. Read the absorbance of each well with an ELISA reader at a wave length of 490–498 nm within 5–8 min of stopping the reaction.. A reference wavelength of 600–650 nm may also be used.

C. Interpretation of Assay Results

1. Average the triplicate readings of NC and PC.

2. Calculate the percent enhancement for PC and each specimen: % Enhancement=(OD in presence of MB40/OD in absence of MB40)×100

3. Calculate:

DV1=OD of NC in absence of MB40+20% OD of PC in absence of MB40

DV2=0.8×% enhancement for PC

4. For the specimen to be HLA-B27 positive it must meet the following requirements:

(a) either OD of untreated specimen is $\geq 2$; or (b) both of the following:

i. OD of specimen in absence of MB40$\geq$DV 1, and ii. % enhancement of specimen$\leq$DV2.

If the specimen % enhancement is between DV2 and 1.5×DV2, the result is indeterminate. If the specimen OD<DV 1, or the specimen enhancement>DV2, then the specimen is HLA-B27 negative.

Following the above procedure, the following results were obtained.

TABLE 1

Comparison of sHLA-STAT ™ B27
with microlymphocytotoxicity.
Overall In-House Study:
685 Specimens from 601 Individuals

| HLA PHENOTYPE* | sHLA-STAT ™ B27 ELISA | | |
|---|---|---|---|
| | B27+ | B27− | IND** |
| B27+ | 154 | 16 | 8 |
| B27− | 5 | 482 | 20 |

*Microlymphocytotoxicity
**Indeterminate: 4.09%
Sensitivity: 90.59%
Specificity: 98.2%
Agreement: 96.8%

A titration was performed to determine the effect of varying the concentration of the enhancing antibody. The assay was performed as described above, but the concentration of MB40.2 antibody in the enhancing solution was varied. The results are shown in FIG. 1. The data show that a large increase in the percent enhancement occurs between 0 and 5 μg/ml MB40.2. The percent enhancement then stays fairly constant as the concentration of antibody is increased.

It is evident from the above results, that the subject method provides a convenient, accurate determination of the presence of an allele, which cannot be specifically bound by an antibody due to cross-reactivity with a second allele. As exemplified with HLA-B7 and B27, the subject method substantially avoids false results, while giving some quantitative and objective indication of the amount of the allele of interest present. The reagents employed are safe, common to many other assays, so that technicians are familiar with the reagents, and can be readily run and the determination made with inexpensive equipment.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for determining the presence of a soluble first HLA antigen in a sample with antibody which cross- reacts with said first and a second HLA antigen, said method comprising:

combining aliquots of said sample with said cross-reacting antibody in first and second containers in the absence and presence of anti-second HLA antigen, respectively; and combining a separate negative control lacking said first and second HLA antigens with said cross-reacting antibody and a separate positive control comprising said second HLA antigen with said cross-reacting antibody wherein separate portions of each control are combined in the absence and presence of anti-second HLA antigen, respectively, wherein the presence of anti-second HLA antigen acts to enhance a signal;

adding a conjugate of antibody and a spectrophotometrically detectable label which antibody of said conjugate binds to a common epitope of said first and second HLA antigens at other than the binding site of said cross-reacting antibody; and determining a signal from said detectable label in said first and second containers and said negative and positive controls;

wherein a signal value is positive for the presence of said first HLA antigen which has both the OD of the sample in the absence of the anti-second HLA antigen$\geq$DV1 and the percent enhancement as a result of the presence of anti-second HLA antigen in the sample$\leq$DV2, wherein DV1 is defined as equal to the OD of the negative control in the absence of anti-second HLA antigen plus a percentage of the OD of the positive control in the absence of anti-second HLA antigen; DV2 is defined as a percentage of the percent enhancement as a result of the presence of anti-second HLA antigen in the positive control, wherein the percentages are selected to avoid false results.

2. A method according to claim 1, wherein said sample is a blood sample.

3. A method according to claim 1, wherein a plurality of samples are tested using microtiler plates.

4. A method according to claim 1, wherein said label is an enzyme and including the additional steps of;

adding enzyme substrate to said containers;

incubating for sufficient time to produce a signal and stopping the enzyme reaction.

5. A method for determining the presence of soluble HLA-B27 in a sample with cross-reacting antibody which cross-reacts with HLA-B7 and -B27, said method comprising:

combining aliquots of said sample with said cross-reacting antibody in first and second containers in the presence and absence of anti-HLA-B7, respectively;

combining a separate negative control lacking said HLA-B7 and -B27 with said cross-reacting antibody and a separate positive control comprising said HLA-B7 with said cross-reacting antibody, wherein separate portions of each control are combined in the absence and presence of anti-HLA-B7, respectively, wherein the presence of said anti-HLA-B7 acts to enhance a signal;

adding a conjugate of a monoclonal antibody and a spectrophotometrically detectable label which antibody of said conjugate binds to a common epitope of HLA-B7 and - B27 antigens; and determining a signal from said detectable label in said first and second containers and said negative and positive controls;

wherein a signal value is positive for the presence of said HLA-B27 which has both the OD of the sample in the absence of the anti-B7 $\geq$ DV1 and the percent enhancement as a result of the presence of anti-HLA-B7 in the sample $\leq$ DV2, wherein DV 1 is defined as equal to the OD of the negative control in the absence of anti-B7 plus a percentage of the OD of the positive control in the absence of anti-B7; DV2 is defined as a percentage of the percent enhancement as a result of the presence of anti-B7 in the positive control, wherein the percentages are selected to avoid false results.

6. A method according to claim 5, wherein said sample is a blood sample.

7. A method according to claim 5, wherein said cross-reacting antibody is a monoclonal antibody having a greater affinity for HLA-B27 than HLA-B7.

8. A method according to claim 5, wherein a plurality of samples are tested using microtiter plates.

9. A method according to claim 5, wherein said label is an enzyme and including the additional steps of:

adding enzyme substrate to said containers;

incubating for sufficient time to produce a signal and stopping the enzyme reaction.

* * * * *